United States Patent
Piva et al.

(10) Patent No.: US 7,258,880 B2
(45) Date of Patent: Aug. 21, 2007

(54) COMPOSITION FOR USE IN ANIMAL NUTRITION COMPRISING A CONTROLLED RELEASE LIPID MATRIX, METHOD FOR PREPARING THE COMPOSITION AND METHOD FOR THE TREATMENT OF MONOGASTRIC ANIMALS

(75) Inventors: Andrea Piva, Bologna (IT); Maurizio Tedeschi, Reggio Emilia (IT)

(73) Assignee: Vetagro S.R.L., Reggio Emilia (IT)

( * ) Notice: Subject to any disclaimer, the term of this patent is extended or adjusted under 35 U.S.C. 154(b) by 463 days.

(21) Appl. No.: 10/608,937

(22) Filed: Jun. 27, 2003

(65) Prior Publication Data
US 2004/0009206 A1    Jan. 15, 2004

(30) Foreign Application Priority Data
Jun. 28, 2002    (IT)    ............ MI2002A1427

(51) Int. Cl.
*A23K 1/18*    (2006.01)
(52) U.S. Cl. ............ 426/98; 2/635; 2/654; 2/807
(58) Field of Classification Search .......... 426/98, 426/61, 89, 99, 105, 2, 635, 654, 807
See application file for complete search history.

(56) References Cited

U.S. PATENT DOCUMENTS

| | | | |
|---|---|---|---|
| 3,692,534 A | | 9/1972 | Ueno et al. |
| 3,930,031 A | | 12/1975 | Kealy |
| 4,197,320 A | | 4/1980 | Betz |
| 4,820,739 A | * | 4/1989 | Ramallo et al. ............ 514/763 |
| 5,204,029 A | * | 4/1993 | Morgan et al. ............ 264/4.4 |
| 5,496,571 A | * | 3/1996 | Blagdon et al. ............ 426/2 |
| 5,741,518 A | * | 4/1998 | Ribier et al. ............ 424/450 |
| 5,897,897 A | * | 4/1999 | Porzio et al. ............ 426/96 |
| 6,217,915 B1 | | 4/2001 | Luchansky et al. |
| 2002/0086090 A1 | * | 7/2002 | Raczek et al. ............ 426/2 |

FOREIGN PATENT DOCUMENTS

| | | |
|---|---|---|
| EP | 0 345 886 | 12/1989 |
| EP | 1 022 023 | 7/2000 |
| WO | WO91/05554 | 5/1991 |

OTHER PUBLICATIONS

Patent Abstracts of Japan, vol. 004, No. 073 (C-012), May 28, 1980 & JP 55037159 A (Nippon Synthetic Chem Ind Co Ltd:The), Mar. 15, 1980.
Patent Abstracts of Japan, vol. 004, No. 019 (C-073), Feb. 16, 1980 & JP 54157921 A (Nippon Synthetic Chem Ind Co Ltd:The), Dec. 13, 1979.
Database WPI, Section Ch, Week 197628, Derwent Publications Ltd., London, GB; AN 1976-53238X, XP002238962 & JP 51061667 A (Nihon Nosan Kog KK), May 28, 1976.
Database WPI, Section Ch, Week 197902, Derwent Publications Ltd., London., GB; AN 1979-03001B, XP002238963 & JP 53136518 A (Ogawa H), Nov. 29, 1978.
Database WPI, Section Ch, Week 197932, Derwent Publications Ltd., London, GB; AN 1979-58797B, XP002238964 & JP 54080439 A (Ogawa H), Jun. 27, 1979.
Database WPI, Section Ch, Week 198628, Derwent Publications Ltd., London, GB; AN 1986-180545, XP002238961 & JP 61115021 A (Kamata M), Jun. 2, 1986.
A. Piva et al.: "Effect of microencapsulation on absorption processes in the pig", Livestock Production Science., vol. 51, No. 1/3, 1997, pp. 53-61, XP002238960, Elsevier Science, Amsterdam., NL, ISSN: 0301-6226.

* cited by examiner

*Primary Examiner*—C. Sayala
(74) *Attorney, Agent, or Firm*—Pearne & Gordon LLP

(57) ABSTRACT

The present invention relates to a composition for use in animal nutrition comprising a controlled release matrix and to a method for preparing said composition. Moreover, the present invention relates to a method for the treatment of monogastric animals in which said composition is used as addition of active substances such as for instance organic acids and/or inorganic acids for preserving and acidifying food for monogastric animals, including swine, sheep, rabbits, birds, horses, pets and humans.

19 Claims, 4 Drawing Sheets

COMPOSITION FOR USE IN ANIMAL NUTRITION COMPRISING A CONTROLLED RELEASE LIPID MATRIX, METHOD FOR PREPARING THE COMPOSITION AND METHOD FOR THE TREATMENT OF MONOGASTRIC ANIMALS

FIELD AND BACKGROUND OF THE INVENTION

The present invention relates to a composition for use in animal nutrition comprising a controlled release matrix and to a method for preparing said composition.

Moreover, the present invention relates to a method for the treatment of monogastric animals in which said composition is used as addition of active substances such as for instance organic acids and/or inorganic acids for preserving and acidifying food for monogastric animals, including swine, sheep, rabbits, birds, horses, pets and humans.

It is known that new-born swine (as also other animal species) have a poor gastric secretion of hydrochloric acid.

The low level of hydrochloric acid anyhow enables the digestion of milk proteins, whereas it is not sufficient for a complete digestion of proteins of a different origin (for instance soybean, potato and fish proteins).

New-born swine therefore have a secretive capacity that is suitable for milk feeding but insufficient when breeding techniques and feeding regulations provide for precocious weanings.

In the pre-weaning stage the fermentation of lactose that is present in milk by means of the autochthonous flora is the best defense against the settling of unwanted microflora.

Weaning strongly reduces the introduction of lactose and animals have to develop other defensive mechanisms in order to contrast the proliferation of pathogenic enterobacteria.

The increasing secretion of gastric hydrochloric acid slowly occurring after weaning creates an unfavorable environment for pathogenic microorganisms entering the intestinal portion.

It is also known that pH in the gastro-intestinal system varies according to the portion taken into consideration.

As a matter of fact, stomach has a pH of 2.0-5.0; duodenum has a pH of 4 to 6; jejunum has a pH of 6.0 to 7.0; cecum has a pH of 6.0 to 6.5; and eventually colon has a pH of 6.5 to 7.0.

It is known about the "barrier" effect of the acid environment within the gastric system, acting as an antibacterial defense so as to limit the proliferation of pathogenic bacteria within animals.

In general the acid environment inhibits the growth of bacterial and fungin cells, and some particular types of acids can also contrast the germination and growth of bacterial spores.

However, a microbial resistance to weak organic acids may arise, which can involve various mechanisms.

As far as bacteria are concerned, there is a deep knowledge on their intrinsic mechanisms of inducible resistance against these compounds.

Preservatives can easily get into the cells of gram-positive bacteria whose intrinsic resistance is relatively low for most of them. An exception consists of acid-resistant bacteria (for instance lactic acid producers), which maintain an efficient metabolism also with relatively low cytoplasmic pH values, thus tolerating the accumulation of organic acids within the cell.

In gram-negative bacteria resistance mechanisms are more complicated.

Resistance mechanisms that can be induced in microorganisms have recently been studied more extensively.

It is known that bacterial cells face a lot of factors of potential stresses in their natural "habitat", such as for instance a very low pH value in the stomach or the physiological presence of high amounts of weak organic acids (volatile fatty acids) in the intestine.

Actually, some pathogenic organisms can develop a tolerance feedback to acids consisting in a complex defense system allowing cells to survive in case pH values should sink up to 3. Furthermore, it has also been observed that a tolerance feedback to weak organic acids occurs after the exposition to a pH value below 3.

Such situation can take place and involve among other things an increase of pathogenicity (minimum infecting dose) of some enterobacteriaceae.

Moreover, some bacteria, such as for instance *Salmonella typhimurium,* can develop a tolerance feedback to acids with pH 3 after a previous exposition to a weak acid with pH 5.

Therefore, there is the need for a composition that can contrast the development and proliferation of pathogenic bacteria and fungi in food and in animals' gastro-intestinal system.

In particular, there is the need for a composition for feeding monogastric animals comprising a controlled release matrix and a selected mixture of active substances, which can contrast the development of unwanted microflora in food.

Furthermore, there is the need for a composition for zootechnical and veterinary use comprising a controlled release matrix and a selected mixture of active substances, which can adjust intestinal microbism so as to contrast the proliferation of unwanted intestinal microflora in animals.

The main aim of the present invention is to provide a composition for feeding monogastric animals comprising a released control matrix and a selected mixture of active substances.

Another aim of the present invention is to provide a method for preparing said composition.

A further aim of the present invention is to provide a particular matrix that can carry and release in a controlled way the components of the selected mixture of active substances within the gastro-intestinal portion of animals including humans.

Finally, a still further aim of the present invention is to provide the use of a matrix that can carry and release a selected mixture of active substances for preparing a composition for treating intestinal dysmicrobism.

These and other aims that will be evident from the following detailed description have been achieved by the Applicant, who has found it useful to prepare a composition for feeding monogastric animals.

SUMMARY OF THE INVENTION

A first object of the present invention is a composition for feeding monogastric animals comprising a controlled release lipid matrix and a mixture of active substances, whose characteristics are disclosed in the appended claims.

Preferably, the composition according to the present invention is in microencapsulated form.

Advantageously, the composition according to the present invention has a wide action spectrum in adjusting bacterial metabolism in feed and in releasing the active substances within animals' gastro-intestinal portion. Moreover, the composition according to the invention has a time-constant activity that goes on also after the animal has ingested the food.

Another object of the present invention is a method for preparing said composition, whose characteristics are disclosed in the appended claims.

DESCRIPTION OF THE PREFEREED EMBODIMENT

The Applicant has improved a particular slow release lipid matrix.

The lipid matrix according to the present invention comprises vegetal triglycerides.

The lipid matrix comprises hydrogenated vegetal triglycerides.

The lipid matrix according to the present invention comprises animal triglycerides or mixtures thereof.

Hydrogenated vegetal triglycerides are chosen from the group comprising: palm butter, sunflower oil, corn oil, rape oil, peanut oil and soybean oil.

Alternatively, mixtures of hydrogenated triglycerides can be used in variable proportions of the single components.

Animal triglycerides are chosen among: bovine tallow and swine lard.

The matrix further comprises particular additives. Said additives are chosen from the group comprising: fumed silica, calcium stearate, magnesium stearate, calcium sulfate.

The additives used enable to increase the viscosity of said matrix and to reduce its permeability.

Preferably, the lipid matrix comprises said additives in an amount of 0.1 to 30% by weight with respect to the total weight of said lipid matrix; for instance 1 to 20%.

The controlled release lipid matrix according to the present invention, into which a particular mixture of active substances is dispersed for preparing a composition for zootechnical and veterinary use, has some advantages.

A first advantage consists in that better rheological properties are obtained thanks to the functional stability to the pressure which said composition will undergo during its use for preparing pre-mixtures or complementary or finished feeds.

The properties of release of active substances are optimized since the dissolution of said matrix within the various gastro-intestinal portions takes place gradually.

As a matter of fact, as a consequence of the attack of digestive secretions the matrix according to the present invention enables to obtain a slow and gradual release of the active substances as a function of time.

For instance, a method for preparing the controlled release matrix provides that said lipid matrix is introduced into a container provided with heating and mixing devices. The container temperature is then brought to a temperature of 80 to 120° C. and the matrix is kept under stirring until it melts.

The melted matrix is then added with the additives. Stirring and temperature are kept until a homogenous mixture is obtained. During this stage emulsifiers may be added to said homogenous mixture.

The Applicant has improved a microencapsulated composition. Said composition is in the physical form of spheres having a diameter of 100 to 2000 microns, in each sphere active substances being incorporated within the matrix and therefore separated from outside.

Said composition comprises a controlled release matrix into which a selected mixture of active substances is dispersed.

In a preferred embodiment according to the present invention the mixture of active substances is a mixture of organic acids, inorganic acids and/or salts thereof.

In another preferred embodiment according to the present invention the mixture of active substances is a mixture of organic acids, inorganic acids and/or salts thereof and a mixture of natural or natural-similar aromatizing agents.

In a further preferred embodiment according to the present invention the mixture of active substances is a mixture of organic acids, inorganic acids and/or salts thereof, a mixture of natural or natural-similar aromatizing agents and/or drugs, such as antibiotics.

Natural or natural-similar aromatizing agents are chosen for instance from mixtures of herbs and plant extracts, oleoresins, essential oils or (generally recognized as safe—GRAS) aromatic substances and fragrances such as natural additives, among which garlic (*Allium sativum*), oregano and the main components of its essential oils, among which carvacrol, p-cymene and y-terpinene. Essential oils are rich in aromatic compounds extracted from plants by means of various processes among which distillation with water or vapor, extractions with solvents or hypercritic extractions. They can be distilled from flowers, seeds, leaves or roots, or from the whole plant.

When these products are extracted and then concentrated, great attention should be paid to the purity of the plant to be extracted, in order to avoid extraction and concentration also of mycotoxins generated by epiphyte fungi or alkaloids of plants that can damage the animals' health.

The chemical composition of essential oils can be highly complex, including also terpenoids, phenolic acids and flavonoids with antioxidant or antimicrobial properties. Flavonoids can also act as chelating agents for metals, such as copper and iron, which are known pro-oxidant agents.

Other examples are sage, rosemary, vanilla.

Beyond the use of natural aromatizers, natural-similar substances can be used, which thanks to their purity degree enable a higher constancy in the formulation.

The microencapsulation of these substances allows to limit the loss of the most volatile components while preparing and storing food and further allows to adjust the release of fragrances and aromatic substances, so as to supply the animal with a stabilized and tasty food and to enable the slow release of these aromatic substances in the gastro-intestinal portion.

The mixture of 5% natural or natural-similar aromatizing agents is present in an amount of 1 to 50% by weight with respect to the total weight of the final composition; preferably of 5 to 15% by weight.

Preferably, the mixture of acids can contain in addition other nutritional components that are physiologically useful for animals.

Preferably, the composition comprises the controlled release matrix in an amount of 40 to 70% by weight with respect to the total weight of the composition.

Preferably, the composition comprises the mixture of organic and/or inorganic acids in an amount of 30 to 60% by weight with respect to the total weight of the composition.

The mixture of acids comprises organic and inorganic acids chosen from the group consisting of: lactic acid, citric acid, fumaric acid, malic acid, sorbic acid, orthophosphoric acid.

Preferably, formic acid is contained in the mixture of acids in an amount of 0.1 to 50% by weight; preferably of 5 to 15% by weight; and salts for instance calcium formate 5 to 15% by weight.

Preferably, lactic acid (absorbed on 50% silica gel) is contained in the mixture of acids in an amount of 0.1 to 50% by weight; preferably of 5 to 15% by weight.

Preferably, citric acid is contained in the mixture of acids in an amount of 0.1 to 60% by weight; preferably of 5 to 15% by weight.

Preferably, fumaric acid is contained in the mixture of acids in an amount of 0.1 to 60% by weight; preferably of 5 to 20% by weight.

Preferably, malic acid is contained in the mixture of acids in an amount of 0.1 to 60% by weight; preferably of 5 to 15% by weight.

Preferably, sorbic acid is contained in the mixture of acids in an amount of 0.1 to 60% by weight; preferably of 5 to 20% by weight; and salts for instance potassium sorbate 5 to 20% by weight.

Preferably, orthophosphoric acid (absorbed on 60% silica gel) is contained in the mixture of acids in an amount of 0.1 to 50% by weight.

The following contains a list of some compositions of the present invention included as a mere nonlimiting example.
1. 12.5% formic acid, 37.5% lactic acid and 50% matrix.
2. 10% citric acid, 20% fumaric acid, 10% malic acid, 1% sorbic acid, 15% orthophosphoric acid and 44% matrix.
3. 8% citric acid, 8% malic acid, 18% fumaric acid, 10% sorbic acid, 8% orthophosphoric acid, 4% mixture of natural and/or natural-similar aromatizing agents and 44% matrix.
4. 35% calcium formate, 10% fumaric acid, 10% sorbic acid and 45% matrix.
5. 14% calcium formate, 7% calcium propionate, 23% fumaric acid, 5% potassium sorbate and 51% matrix.
6. 32% calcium formate, 5% calcium propionate, 8% potassium sorbate, 5% mixture of natural and/or natural-similar aromatizing agents and 50% matrix.
7. 20% fumaric acid, 10% malic acid, 10% citric acid, 10% orthophosphoric acid and 50% matrix.
8. 34% calcium formate, 1% calcium propionate, 15% potassium sorbate and 50% matrix.

The composition according to the present invention has some advantages.

An advantage consists in a slow release of the substances dispersed into the matrix within the gastro-intestinal portion of the various animal species they are meant for.

Tests have shown that there is no immediate release within the gastric system due to pH change (for very acid pH values), but a progressive release within the jejunum due to the action of digestive enzymes.

Another object of the present invention is a method for preparing the composition comprising a controlled release matrix, in which the matrix prepared as described above is added with the active substances. The whole is homogenized at a temperature of 55 to 70° C. Then the suspension is sprayed in a cold room at a temperature below 15° C.

A further object of the present invention is the use of said composition as such or in the preparation of feeds and/or pre-mixtures to be used in the zootechnical and veterinary field for feeding birds, swine and young calves (whose rumen is not working yet).

Practically, the composition according to the invention can protect and carry the active substances dispersed therein. For instance, said active substances include drugs such as: antibiotics, vaccines, anti-inflammatories and antihistamines.

Said active substances and/or drugs are released within the intestine.

A preferred embodiment relates to the use of said composition comprising drugs for preventing and/or treating pathologies in intensive breeding farms.

Experimental Part

The study aimed at verifying in vivo the effectiveness of the protection given by the composition comprising a controlled release matrix on the dynamics of release of protected molecules, for instance sorbic acid and essential oils, within the various portions of the gastro-intestinal system, checking at the same time possible interferences of said released molecules on the development of fermentations due to microorganisms.

The control on the content collected from the various portions of the gastro-intestinal system allowed to find out the presence of the molecules concerned in microencapsulated form (sorbic acid and essential oils) in concentrations progressively decreasing from stomach to colon for sorbic acid and to jejunum for essential oils.

Sorbic acid undergoes a reduction of its concentration from proximal jejunum as far as colon, whereas the protective effect of essential oil is present as far as distal jejunum.

The same formulation containing sorbic acid and essential oils in non-microencapsulated form did not enable the detection of the aforesaid molecules beyond pylorus.

The type of protection used results in a precise late effect because it helps to modify the availability of said protected molecules, sorbic acid and essential oils, within the various gastro-intestinal portions that were controlled. The development of fermentations is clearly affected by treatments.

The following experimental pattern was used:
1. Control group: subjects fed with a conventional diet without addition of drugs or of the substances under study. At the end of the experimental period five subjects with a living weight corresponding to the average of the group they belonged to, were chosen to be killed. Various gastro-intestinal portions (stomach, proximal and distal jejunum, ileum, cecum, sigmoid colon) were taken from the animals just killed.
2. Group treated with a slow release microencapsulated composition according to the present invention: subjects fed with a conventional diet, whose composition was the same as for control group, added with an amount of 0.5% in a period of 0-15 test days. At the end of the experimental period five subjects with a living weight corresponding to the average of the group they belonged to, were chosen to be killed. Various gastro-intestinal portions (stomach, proximal and distal jejunum, ileum, cecum, sigmoid colon) were taken from the animals just killed.
3. Group treated with a (non-microencapsulated) mixture reproducing the composition according to the present invention: subjects fed with a conventional diet, whose composition was the same as for control group, added with an amount of 0.5% in a period of 0-15 test days. At the end of the experimental period five subjects with a living weight corresponding to the average of the group they belonged to, were chosen to be killed. Various gastro-intestinal portions (stomach, proximal jejunum, distal jejunum, ileum, cecum, sigmoid colon) were taken from the animals just killed.

During the whole test period the animals were fed ad libitum and could drink water freely.

Analyses

The analyses on animal food were carried out in accordance with the provisions contained in the body of analytical methods for zootechnical food.

The gastro-intestinal contents were tested in order to determine humidity, volatile fatty acids, ammonia, essential oil and sorbic acid.

The analysis on humidity was carried out in an oven heated to 80° C. until a constant sample weight was obtained (around 20 hours). The analysis on fatty acids and volatile compounds were carried out in accordance with the method described by Fussel R. J. and Mc Cailey D. V. (*Analist,* 112, 1213-1216; 1987). The analyses for determining essential oil and sorbic acid were carried out in accordance with the following methods:

Operate under indirect light.

Weigh in centrifuge tube 50 g of sample, add 5 ml of 5% trichloroacetic acid, centrifuge for 10 min at 11000 RPM at 4° C., then filter on paper filter. Transfer 20 ml of filtrate in distillation Kijedahl tube, add 10 ml of HCl 3 N, distillate in vapor stream for 12 min and measure distillate volume. Filter about one ml of distillate with 0.45 micron filters and inject 30 μl in HPLC.

RP-18 column (Merck) eluting mixture $H_2O:CH_3OH=75:25$ with a flow of 1 ml/min, UV detector 1575 (Jasco) operating at 245 nanometers; peak output about 7.4 min. Detectability limit for sorbic acid: 0.05 mg/kg referred to initial sample. Recovery 96.1±2.4%. All data collected during the test were statistically processed.

A variance analysis was carried out using Anova procedure with Wartler test and Newmanchius post-test. The differences were regarded as significant with $P<0.05$.

Results

Evaluation of analytical data concerning controls of gastro-intestinal content of various groups. The presence of sorbic acid is absent in the samples taken from control group, whereas its presence can be detected in the various gastro-intestinal portions of the group treated with the composition according to the present invention and with the mixture reproducing the (non-microencapsulated) composition according to the present invention.

The content of sorbic acid is high in the samples of stomach, with similar values in groups treated with the composition according to the present invention and with the mixture reproducing the (non-microencapsulated) composition according to the present invention, whereas there is a great difference starting from the first intestine portion (proximal jejunum)

As far as the group treated with the composition according to the present invention is concerned, the content of sorbic acid decreases very slowly in the various intestinal portions and a small amount is still present in colon; as far as the intestinal portions of the group treated with the mixture reproducing the (non-microencapsulated) composition according to the present invention are concerned, sorbic acid is present in small amounts only in the first intestine portion (proximal jejunum). The presence of essential oil was detected in a significant amount and with little variation in stomach samples of the group treated with the compositions according to the present invention and with the mixture reproducing the (non-microencapsulated) composition according to the present invention, whereas it is absent in all samples of subjects belonging to the control group.

In the group treated with the composition according to the present invention the presence of essential oil can be detected in proximal and distal jejunum, but is absent in the following intestinal portions. Conversely, in the group treated with the mixture reproducing the (non-microencapsulated) composition according to the present invention, essential oil is present only in samples taken from stomach (concentrations that are similar to those of the group treated with the composition according to the present invention)

Conclusions Drawn from the Tests

The type of protection used results in a precise late effect because it helps to modify the analytical detectability, and therefore the availability, of protected molecules, above all sorbic acid and essential oil, within the various gastro-intestinal portions that were controlled.

As a consequence the microorganisms that are present in the various portions of the gastro-intestinal system affect the development of fermentative processes.

TABLE 1 analytical features of diets compared during the period 0-15 days (data in percentage of dry matter);

|  |  | Control | Micro-encapsulated composition | NON-micro-encapsulated composition |
|---|---|---|---|---|
| Dry matter | % | 90.49 | 90.59 | 90.47 |
| Raw protides | % | 18.32 | 17.94 | 18.27 |
| Raw lipids | % | 6.61 | 6.69 | 6.49 |
| Raw fiber | % | 3.81 | 4.03 | 3.01 |
| Ashes | % | 6.66 | 6.59 | 6.76 |
| Starch | % | 45.64 | 44.40 | 44.46 |
| Digestible ergy[1] | En-kcal/kg | 3848 | 3846 | 3854 |
| Net Energy[2] | kcal/kg | 2755 | 2755 | 2753 |

[1]According to Whittemore (1980);
[2]According to Noblet (1994)

Figure 1:
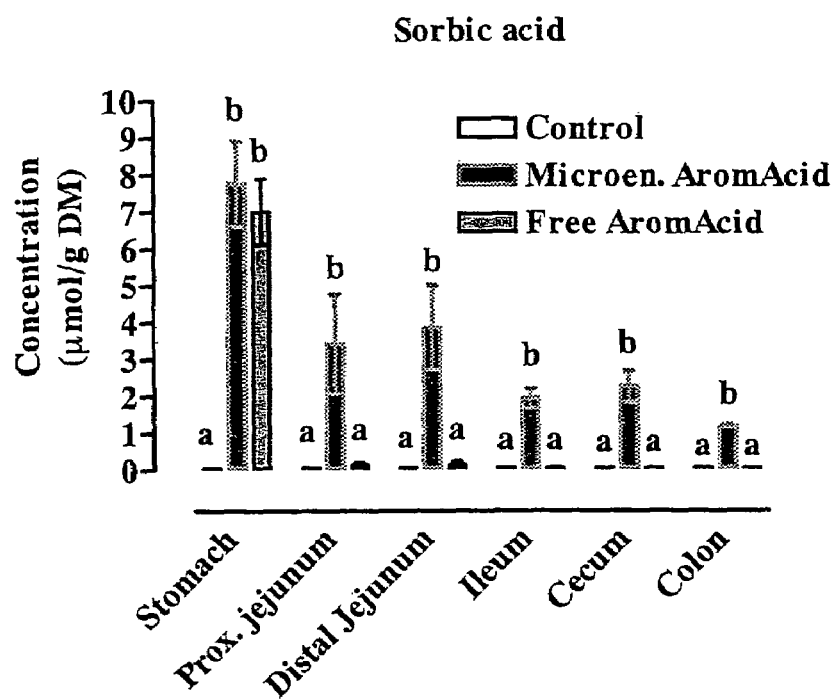
FIG. 1: concentration of sorbic acid micro-moles/gram of dry matter in various gastro-intestinal portions.
Figure 2:
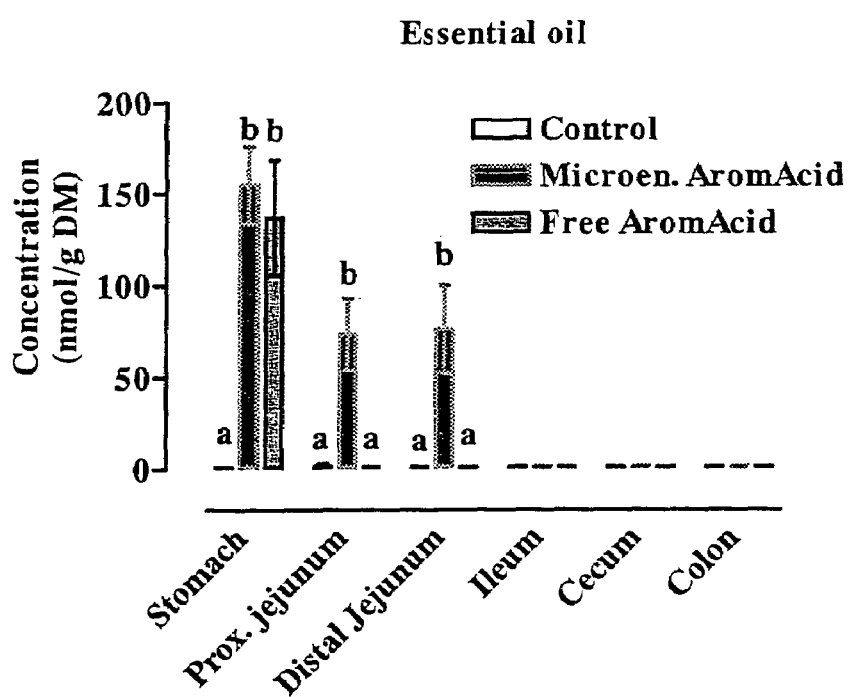
FIG. 2: concentration of essential oil nano-moles/gram of dry matter in various gastrointestinal portions.
Figure 3:
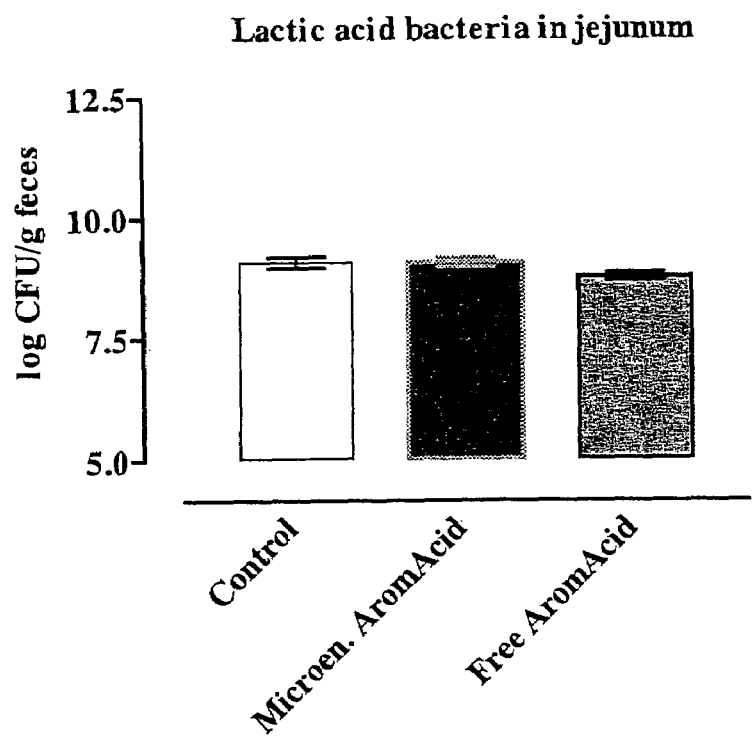
FIG. 3: concentration of lactic acid bacteria in jejunum expressed as log CFU/g of feces in the three groups used.
Figure 4:
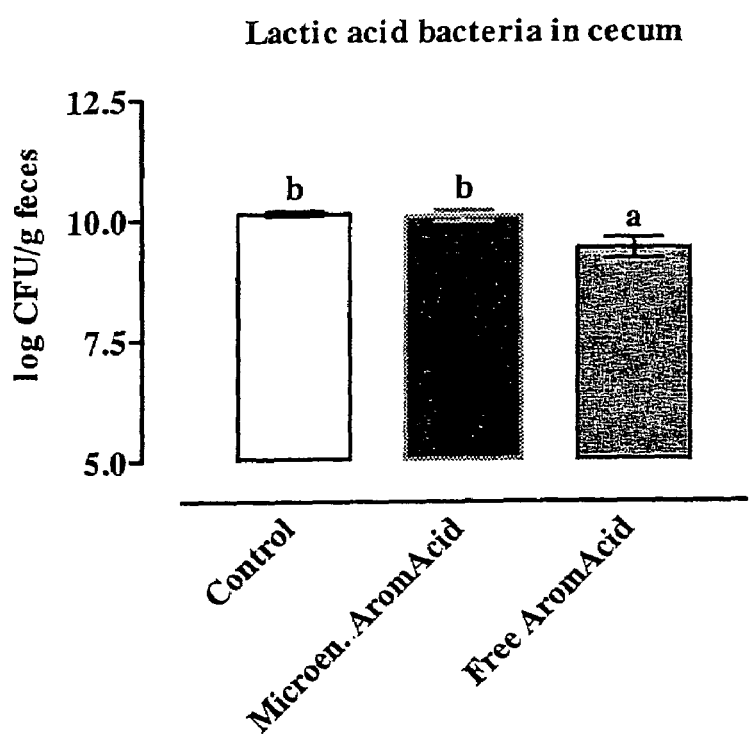
FIG. 4: concentration of lactic acid bacteria in cecum expressed as log CFU/g of feces in the three groups used.
Figure 5:
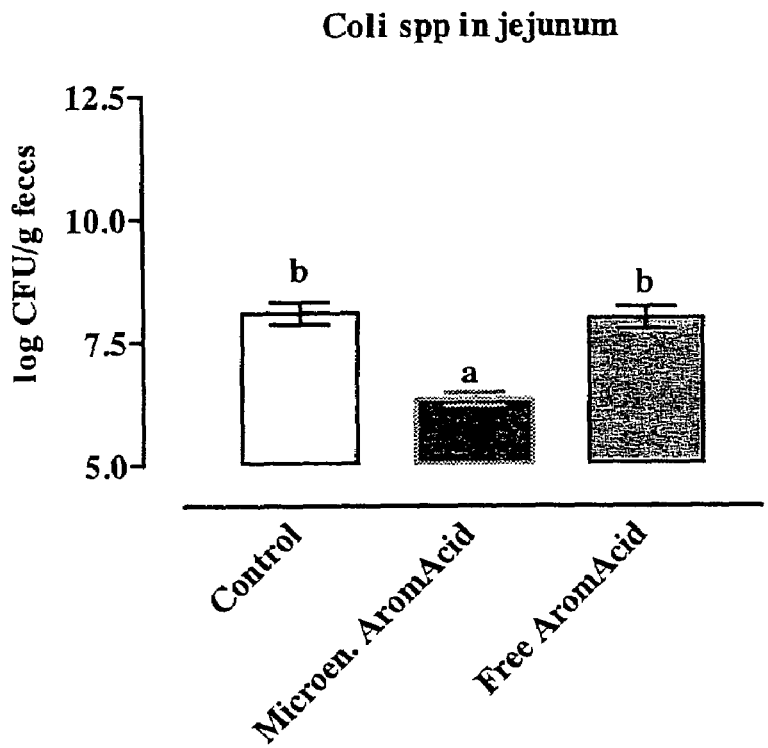
FIG. 5: concentration of Coli spp. in jejunum expressed as log CFU/g of feces in the three groups used.
Figure 6:
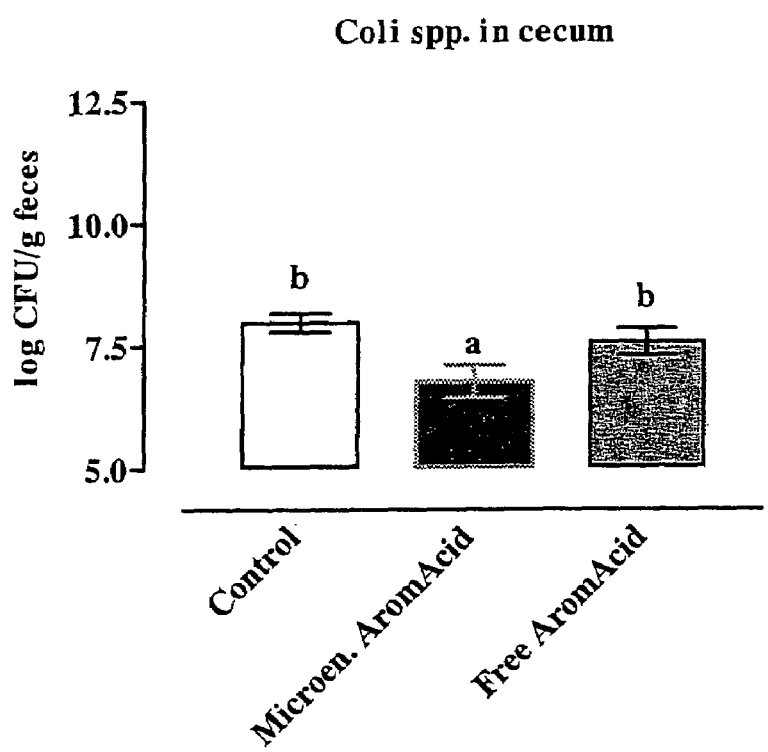
FIG. 6: concentration of Coli spp. in cecum expressed as log CFU/g of feces in the three groups used.
Figure 7:
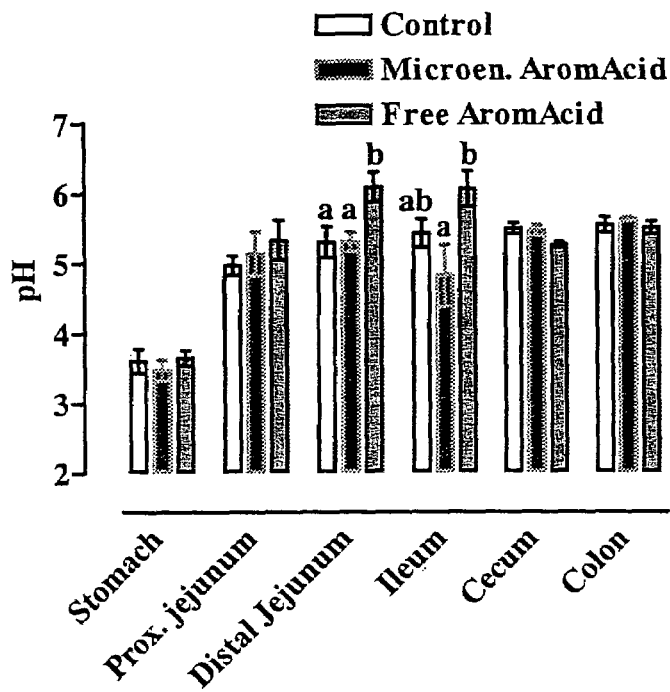
FIG. 7: pH development in various gastro-intestinal portions of the three groups used.
Figure 8:
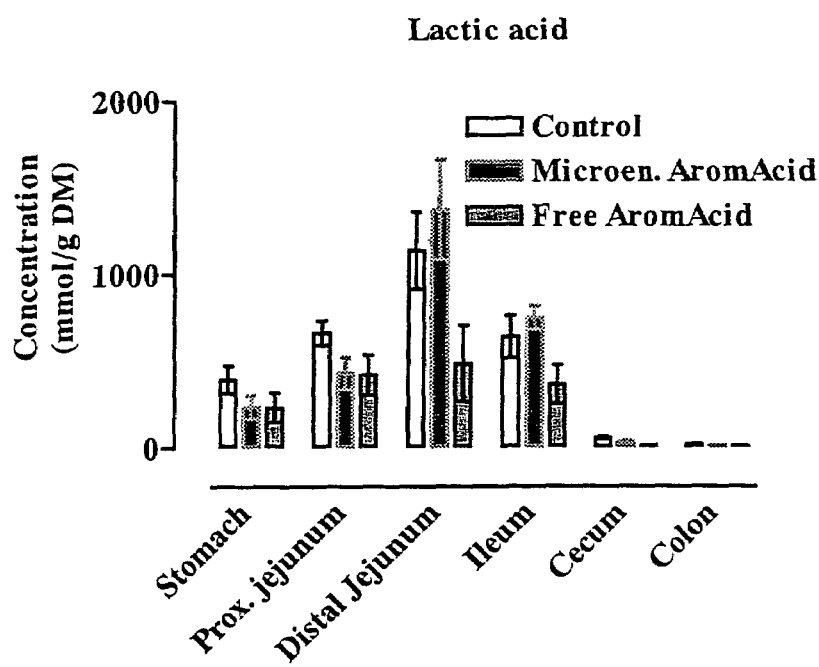
FIG. 8: concentration of lactic acid expressed as nano-moles/gram of dry matter in various gastro-intestinal portions.

The invention claimed is:

1. A composition for feeding monogastric animals comprising a controlled release lipid matrix and a mixture of active substances incorporated within the matrix, where:
   the controlled release lipid matrix consists of (a) at least one hydrogenated vegetable triglyceride selected from the group consisting of: palm butter, sunflower oil, corn oil, rape oil, peanut oil and soybean oil or (b) animal triglycerides selected from the group consisting of: bovine tallow and swine lard;
   the mixture of active substances consists of at least one organic acid and at least one aromatizing agent wherein the organic acid is selected from the group consisting of:
   formic acid in an amount of 0.1 to 50% by weight, with respect to the weight of the composition;

lactic acid in an amount of 0.1 to 50% by weight, with respect to the weight of the composition;

citric acid in an amount of 0.1 to 60% by weight, with respect to the weight of the composition;

fumaric acid in an amount of 0.1 to 60% by weight, with respect to the weight of the composition;

malic acid in an amount of 0.1 to 50% by weight, with respect to the weight of the composition;

and sorbic acid in an amount of 0.1 to 60% by weight, with respect to the weight of the composition;

and the aromatizing agent is selected from the group consisting of natural and natural-identical aromatizing agents which is further selected from the group consisting of: mixtures of herbs, extracts from plants, oleoresins, essential oils, aromatizers and natural fragrances.

2. The composition according to claim 1, wherein said organic acids are present in form of salts.

3. The composition according to claim 2, wherein said salts of organic acids are selected from the group consisting of:

calcium formate in an amount of 5 to 35% by weight, with respect to the weight of the composition;

and potassium sorbate in an amount of 5 to 20% by weight, with respect to the weight of the composition.

4. The composition according to claim 1, wherein said composition is microencapsulated and is in the physical form of spheres having a diameter of 100 to 2000 microns.

5. The composition according to claim 1, wherein said composition further comprises orthophosphoric acid in an amount of 0.1 to 50% by weight, with respect to the weight of the composition.

6. A method for preparing a composition according to claim 1 comprising the following stages:

place an homogenous mass comprising a melted lipid matrix and additives in a container;

disperse into said homogenous mass a mixture of active substances consisting of at least one organic acid and/or salts thereof and at least one aromatizing agent; and spray in a cold room the mass obtained in the previous stage.

7. The method according to claim 6, wherein said lipid matrix consists of at least one hydrogenated vegetable triglyceride selected from the group consisting of: palm butter, sunflower oil, corn oil, rape oil, peanut oil and soybean oil.

8. The method according to claim 6, wherein said organic acids are selected from the group consisting of:

formic acid in an amount of 0.1 to 50% by weight, with respect to the weight of the composition;

lactic acid in an amount of 0.1 to 50% by weight, with respect to the weight-of the composition;

citric acid in an amount of 0.1 to 60% by weight, with respect to the weight of the composition;

fumaric acid in an amount of 0.1 to 60% by weight, with respect to the weight of the composition;

malic acid in an amount of 0.1 to 50% by weight, with respect to the weight of the composition;

and sorbic acid in an amount of 0.1 to 60% by weight, with respect to the weight of the composition.

9. The method according to claim 6, wherein the aromatizing agent is selected from the group consisting of natural and natural-identical aromatizing agents which is further selected from the group consisting of: mixtures of herbs, extracts from plants, oleoresins, essential oils, aromatizers and natural fragrances.

10. The method according to claim 6, wherein said lipid matrix consists of animal triglycerides selected from the group consisting of:bovine tallow and swine lard.

11. The method according to claim 8, wherein said organic acids are present in form of salts.

12. The method according to claim 11, wherein said salts of organic acids are selected from the group consisting of:

calcium formate in an amount of 5 to 35% by weight, with respect to the weight of the composition;

and potassium sorbate in an amount of 5 to 20% by weight, with respect to the weight of the composition.

13. The method according to claim 6, wherein said composition is microencapsulated and is in the physical form of spheres having a diameter of 100 to 2000 microns.

14. The method according to claim 6, wherein said composition further comprises orthophosphoric acid in an amount of 0.1 to 50% by weight, with respect to the weight of the composition.

15. A method for contrasting the development of bacteria or pathogenic fungi in animals' gastro-resistant system comprising a step in which monogastric animals are fed with a composition comprising a controlled release lipid matrix and a mixture of active substances wherein:

the controlled release lipid matrix comprises at least one hydrogenated vegetable triglyceride;

the mixture of active substances comprises at least one organic acid and at least one aromatizing agent selected from the group consisting of natural and natural-identical aromatizing agents.

16. The method according to claim 15 wherein said hydrogenated vegetable triglyceride is selected from the group consisting of: palm butter, sunflower oil, corn oil, rape oil, peanut oil and soybean oil.

17. The method according to claim 15, wherein said organic acid is selected from the group consisting of:

formic acid in an amount of 0.1 to 50% by weight, with respect to the weight of the composition;

lactic acid in an amount of 0.1 to 50% by weight, with respect to the weight of the composition;

citric acid in an amount of 0.1 to 60% by weight, with respect to the weight of the composition;

fumaric acid in an amount of 0.1 to 60% by weight, with respect to the weight of the composition;

malic acid in an amount of 0.1 to 50% by weight, with respect to the weight of the composition;

and sorbic acid in an amount of 0.1 to 60% by weight, with respect to the weight of the composition.

18. The method according to claim 15, wherein said aromatizing agent is selected from the group consisting of: mixtures of herbs, extracts from plants, oleoresins, essential oils, aromatizers and natural fragrances.

19. The method according to claim 15, wherein the intestinal microbism is equilibrated in order to contrast the proliferation of unwanted intestinal microflora in the animals.

* * * * *